(12) United States Patent
Brooks et al.

(10) Patent No.: US 7,691,905 B2
(45) Date of Patent: Apr. 6, 2010

(54) INHIBITION OF MELANOGENESIS AND MELANOMA METASTASIS WITH P-AMINOBENZOIC ACID (PABA)

(75) Inventors: Peter C. Brooks, Carmel, NY (US); Danielle Morais, Bedford Hills, NY (US); Dorothy Rodriguez, Pequannock, NJ (US)

(73) Assignee: New York University, New York, NY (US)

( * ) Notice: Subject to any disclaimer, the term of this patent is extended or adjusted under 35 U.S.C. 154(b) by 1093 days.

(21) Appl. No.: 10/746,206

(22) Filed: Dec. 23, 2003

(65) Prior Publication Data

US 2004/0167222 A1 Aug. 26, 2004

Related U.S. Application Data

(60) Provisional application No. 60/436,394, filed on Dec. 24, 2002.

(51) Int. Cl.
*A61K 31/192* (2006.01)

(52) U.S. Cl. .................................................. 514/557

(58) Field of Classification Search .................. 514/557
See application file for complete search history.

(56) References Cited

U.S. PATENT DOCUMENTS

| 3,019,165 | A | * | 1/1962 | Mansor | 514/161 |
| 4,762,705 | A | * | 8/1988 | Rubin | 424/85.4 |
| 5,532,275 | A | | 7/1996 | Grumet | |
| 5,567,420 | A | * | 10/1996 | McEleney et al. | 424/60 |
| 6,080,777 | A | * | 6/2000 | Schiff | 514/449 |
| 6,255,290 | B1 | * | 7/2001 | von Borstel et al. | 514/45 |
| 6,368,598 | B1 | * | 4/2002 | D'Amico et al. | 424/181.1 |
| 6,403,565 | B1 | | 6/2002 | von Borstel et al. | |

FOREIGN PATENT DOCUMENTS

| EP | 0100651 | 2/1984 |
| WO | WO-9961038 | 12/1999 |

OTHER PUBLICATIONS

Hardman, J. G., Editor-in-chief of Goodman 7 Gilman's the Pharmacological Basis of Therapeutics, Ninth Edition, pp. 1225-1230, 1996.*
Zbytniewski, Z. et al., Arch Geschwulstforsch 1977: 47:400-404.*
Myderse et al. Oral therapy for Peyronie's disease. International Journal of Impotence Research, 2002, col. 14, pp. 340-344.*
Hodi et al. Phase II study of paclitaxel and carboplatin for malignant melanoma. Am. J. Clin. Oncol., 2002, vol. 25, pp. 283-286.*
Bafaloukos et al. Temozolomide in combination with docetaxel in patients with advanced melanoma: a phase II study of the hellenic cooperative oncology group. Journal of Clinical Oncology, 2002, vol. 20, pp. 420-425.*
Esposito et al. Effect of para-aminobenzoic acid on the pharmacokinetics and urinary excretion of cis-diamminedichloroplatinum(II) in rats. Anticancer Research, 1995, vol. 15, pp. 2541-2547.*
Slominski et al. Inhibition of Melanogenesis for Melanoma Therapy. The Journal of Investigative Dermatology, 1994, vol. 103, p. 742.*
Hughes, C.G. Oral PABA and Vitiligo. Journal of the American Academy of Dermatology, 1983, vol. 9, No. 5, p. 770.*
Hodi et al. Phase II study of paclitaxel and carboplatin for malignant melanoma. Am. J. Clin. Oncol., 2002, vol. 25, No. 3, pp. 283-286.*
Seegenschmiedt et al. Int. J. Radiat. Oncol. Biol. Phys., 1999, vol. 44, No. 3, pp. 607-618 (Abstract attached).*
Sausville et al. Cancer Research, 2006, vol. 66, pp. 3351-3354.*
Johnson et al. British J. of Cancer, 2001, 84(10):1424-1431.*
Walker et al. Melanoma Res., 2005, vol. 15, No. 5, pp. 453-459 (Abstract attached).*
Zimpfer-Rechner et al. Melanoma Res., 2003, vol. 13, No. 5, pp. 531-536 (Abstract attached).*
Gause et al. Cancer Invest., 1998, vol. 16, No. 6, pp. 374-380 (Abstract attached).*
Ahmann et al. Clin. Pharmacol. Ther., 1976, vol. 19, No. 6, pp. 821-824 (Abstract attached).*
Creagan et al. J. Clin. Oncol., 1999, vol. 17, No. 6, pp. 1884-1890.*
Brooks et al., Cell 1994;79:1157-1164.
Chapman et al., Melanoma Res 2002;12:381-387.
Holt GA, Food & Drug Interactions 1998;170.
Flaherty et al., Semin Oncol 2002;29:446-455.
Ichihasyhi et al., Br J Dermatol 2001;144:745-750.
Kinnaert et al., Radiation Res 2000;154:497-502.
Mauceri et al., Cancer Chemother Pharmacol 2002;50:412-418.

(Continued)

*Primary Examiner*—James D Anderson
(74) *Attorney, Agent, or Firm*—Darby & Darby P.C.

(57) ABSTRACT

The present invention relates to the inhibition of melanogenesis with para-aminobenzoic acid (PABA) and its use in treating melanotic cancer.

4 Claims, 12 Drawing Sheets

OTHER PUBLICATIONS

Petitclerc et al., J Biol Chem 2000:275:8051-8061.
Prota et al., Melanoma Res 1994;4:351-358.
Riley PA, Eur J Cancer 1991;27:1172-1177.
Slominski et al., Anti-Cancer Res 1998;18:3709-3716.
Young et al., Int J Cancer 2003;103:38-44.
Zbytniewski et al., Arch Geschwulstforsch 1977;47:400-404.
Lorincz, A., L. "Studies on the inhibition of melanin formation". Journal of Investigative Dermatology, Dec. 1950, pp. 425-432.
Iida, et al, 1995. "Potent Inhibitors of Tyrosinase Activity and Melanin Biosynthesis from Rheum Officinale". Planta Medica 61: 425-428.
Priestman, T., J., 1979. "Interferon: an anti-cancer agent?" Cancer Treatment Reviews 6: 223-237.
Gilchrest, et al, 1999. "The Pathogenesis of Melanoma Induced by Ultraviolet Radiation". New England Journal of Medicine 340(17): 1341-1347.

* cited by examiner

FIGURE 1
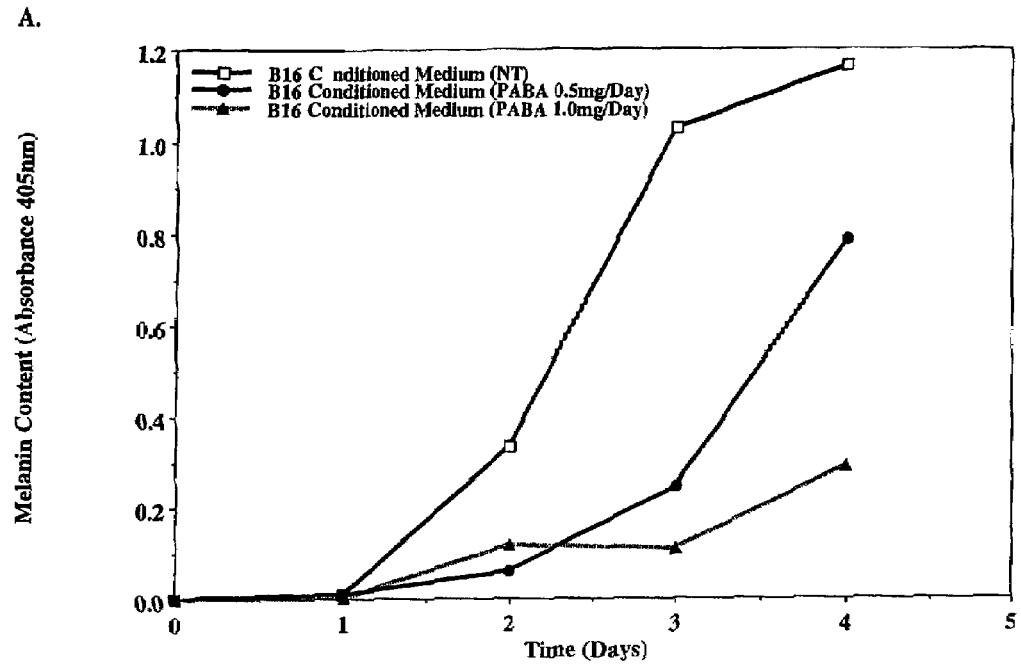
A.
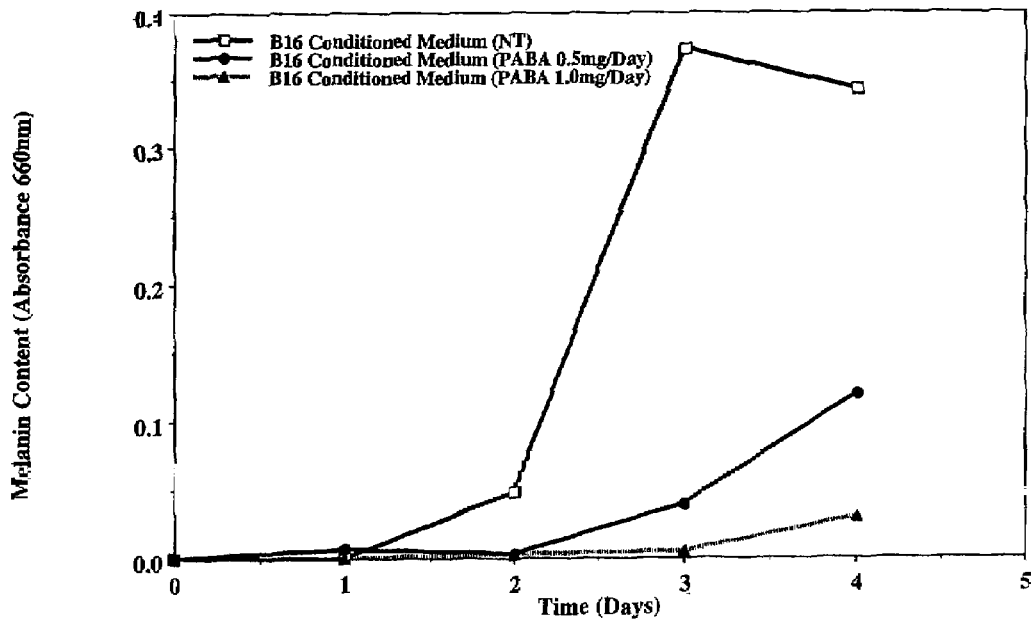
B.

Effects of PABA on Tyrosinase Activity

Effects of PABA on B16 Melanoma Tumor Growth

Effects of 10Gy of Ionizing Radiation on B16 F10 Cell Proliferation in the Presence of Absence of PABA

INHIBITION OF MELANOGENESIS AND MELANOMA METASTASIS WITH P-AMINOBENZOIC ACID (PABA)

The application claims priority under 35 U.S.C. §119(e) to U.S. provisional patent application Ser. No. 60/436,394 filed on Dec. 24, 2002. The entire contents of this provisional application is hereby incorporated by reference in its entirety.

GOVERNMENT SUPPORT

This work was supported in part by NIH/NCI grant ROI CA91645. Pursuant to the terms of that grant, the federal government may have certain rights to this invention.

FIELD OF THE INVENTION

The present invention relates to the inhibition of melanogenesis with para-aminobenzoic acid (PABA) and its use in treating melanotic cancer.

BACKGROUND OF THE INVENTION

Melanoma

The incidence of melanoma in most developed countries has risen faster, over the past 50 years, than any other cancer type. (Houghton A N, (2002) *Cancer Cell;* 2:275-278.) Approximately 45,000 new cases of melanoma are diagnosed each year in the United States, of which about 20% will eventually die secondary to metastatic disease. (Buzaid, A C. (2002) *Crit Rev Ocol Hematol* 44:103-108.) The prognosis for treatment of advanced melanoma is poor, with patient survival dictated primarily by the pace of progress of the disease. (Buzaid, supra.) Surgical intervention remains the most effective treatment option, but only if the disease is diagnosed and treated in its earliest stages. (Molife R et al. (2002) *Crit Rev Oncol Hematol* 44:81-102.) Hence, survival chances are excellent if melanoma is diagnosed and surgically removed in its earliest stages. Each successive stage of disease progression, however, witnesses a significant drop in the chance for survival as the risks of relapse and recurrence increase. (Molife et al, supra.) Thus, there is a need for new, more effective methods of treatment that are distinct from surgical intervention or enhance the efficacy of surgical intervention.

Clinical response rates to treatment are typically lower in patients with melanoma than in patients with other cancers. Clinical trials have shown malignant melanoma to be highly resistant to both chemotherapy as well as radiation treatment. A durable response rate of only about 10% was observed following current treatment modalities. (Flaherty L E et al. (2002) *Semin Oncol* 29:446-455.) An evaluation of biochemotherapy in previously treated patients documented a 6% response rate. (Chapman, et al. (2002) *Melanoma Res.* 12:381-387.)

The lack of therapeutic response to the existing treatment protocols for melanoma, is due largely to its cellular, biochemical, and molecular origins. (Ichihasyhi N et al. (2001) *Br J Dermatol* 144:745-750; Heere-Ress et al. (2002) *Int J Cancer* 99:29-34; Sinha P et al. (2000) *Electrophoresis* 21:3048-3057.) Melanomas arise from a very specific cell lineage: they are the product of the malignant conversion of melanocytes, which are themselves derived originally from mesenchymal neural crest cells. In contrast, carcinomas arise from the malignant conversion of epithelial cells. Furthermore, melanomas are not sex hormone dependent, while many carcinomas are (e.g., androgen-dependent prostate cancer and estrogen-dependent breast). Additionally, melanomas carry out the process of melanogenesis, while carcinomas exhibit this process rarely, if ever. One or more of the characteristic properties of melanomas must account for the resistance of melanomas to existing treatment protocols.

Melanogenesis

Melanogenesis is the process of synthesizing of melanin, which is responsible for cell pigmentation. Melanocytes, located in the skin, hair follicles, stria vascularis of the inner ear and uveal tract of the eye, are the cells of origin for melanomas and exhibit melanogenesis. Melanogenesis is a complex biochemical process initiated by the hydroxylation of the amino acid L-tyrosine, which results in the formation of L-dihydroxyphenylalanine (L-DOPA). L-DOPA is converted, in turn, to Dopachrome by the action of a specific melanocyte-associated enzyme: tyrosinase. Further oxidation and reduction reactions ultimately convert Dopachrome to melanin.

Studies have indicated that melanogenesis is associated with the enhanced resistance of pigmented melanoma cells to radiation therapy and to chemotherapy. (Kinnaert E et al. (2000) *Radiation Res* 154:497-502; Slominski A et al. (1998) *Anti-Cancer Res* 18:3709-3716.) These treatments are thus rendered ineffective against melanotic melanoma. A method to block melanogenesis would provide a clinically useful approach to render melanoma cells more sensitive to both chemotherapy and radiotherapy.

Studies have also shown that many of the intermediate products produced during melanogenesis have toxic effects. (Slominski A et al. (1998), supra; Riley P A (1991) *Eur J Cancer* 27:1172-1177; Prota G et al. (1994) *Melanoma Res* 4:351-358.) Intermediates of melanogenesis can contribute to, for example, immunosuppression, fibrosis, and mutagenesis. Inhibition of melanogenesis will therefore enhance the efficacy of cancer treatments that require participation of the host's immune system, e.g., the killing of melanoma cells damaged by radiation or chemotherapy.

para-Aminobenzoic Acid para-Aminobenzoic acid (PABA) has been commonly used in sunscreens for its capacity to absorb ultraviolet radiation. PABA has also been used in clinical trials for the treatment of connective tissue diseases (e.g. scleroderma; dermatomyositis) and in combination with salicylates for the treatment of rheumatic fever. U.S. Pat. No. 6,368,598 (the '598 patent) suggested the use of PABA as a non-essential part of a linking group in a drug complex for the treatment of prostate cancers. As set forth in the '598 patent, the function of PABA is to act as a leaving group that is separated from the cytotoxic therapeutic portion of the drug complex by the action of enzymes present at the site of the intended therapeutic action. There is no suggestion, however, that PABA has any anti-tumor activity or other therapeutic function on prostate or other types of cancer. According to Holt, PABA can increase methotrexate levels, activity, and side effects. (Holt GA (1998) *Food & Drug Interactions.* Chicago: Precept Press, 170.)

para-Aminomethylbenzoic acid (PAMBA), a methylated derivative of PABA, has been found to be useful as a proteinase inhibitor for reducing the invasiveness of transplantable melanoma metastases in hamsters (Zbytniewski Z, et al. (1977) *Arch Geschwulstforsch* 47:400-404). The action of PAMBA is to inhibit proteolysis by extracellular proteases, thus preserving the extracellular matrix as a physical barrier that reduces the invasiveness of cancer cells. Reducing invasiveness, however, does not inhibit the growth of an established metastatic tumor. There is no suggestion therefore that PAMBA inhibits the growth of primary or metastatic melanoma. Nor is there any suggestion that PAMBA inhibits melanogenesis, or that it can enhance the effect of radiation or the activity of chemotherapeutic agents known to be useful in treating melanoma.

Accordingly, primary and metastatic melanoma continue to be difficult to treat with existing therapies. There is therefore a continued need for new effective treatments for these conditions. It has now been surprisingly discovered that PABA acts as a potent inhibitor of melanogenesis and can be used to treat melanoma effectively when administered alone or in combination with other anti-cancer modalities such chemotherapy and radiation. This finding is surprising because melanoma has different cellular origins from other cancers, including other skin cancers, melanoma is known to be highly resistant to treatments such as chemotherapy and radiation, and because the concentrations of PABA that inhibited melanoma cell growth in vitro and in vivo were found to have the opposite effect of enhancing growth of a lung carcinoma.

SUMMARY OF THE INVENTION

The present invention provides a method of inhibiting melanogenesis by administering an effective amount of PABA. In certain embodiments, the invention provides methods of treatment for primary and metastatic melanotic cancer by administering an effective amount of PABA. In treating the aforementioned cancers, PABA may be administered alone as the sole therapeutic agent or, in combination with one or more additional therapies, such as, for example radiation therapy or chemotherapy with one or more chemotherapeutic agents. In one embodiment the invention provides a method for treating metastatic malignant melanoma by administering a combination of PABA, carboplatin, and paclitaxel.

Treatment of metastatic melanotic cancer with PABA may be achieved by any mechanism, e.g., by preventing the growth of melanotic cancer cells or by reducing the invasiveness of melanoma cells, e.g., by proteinase inhibition.

BRIEF DESCRIPTION OF THE DRAWINGS

FIG. 1 shows the effect of PABA on melanin levels secreted in DMEM medium in which B16 melanoma cells were cultured alone or in the presence of PABA. Melanin levels were determined by absorbance at 405 nm wavelength (A) and absorbance at 660 nm wavelength (B).

DETAILED DESCRIPTION OF THE INVENTION

Figure 2:
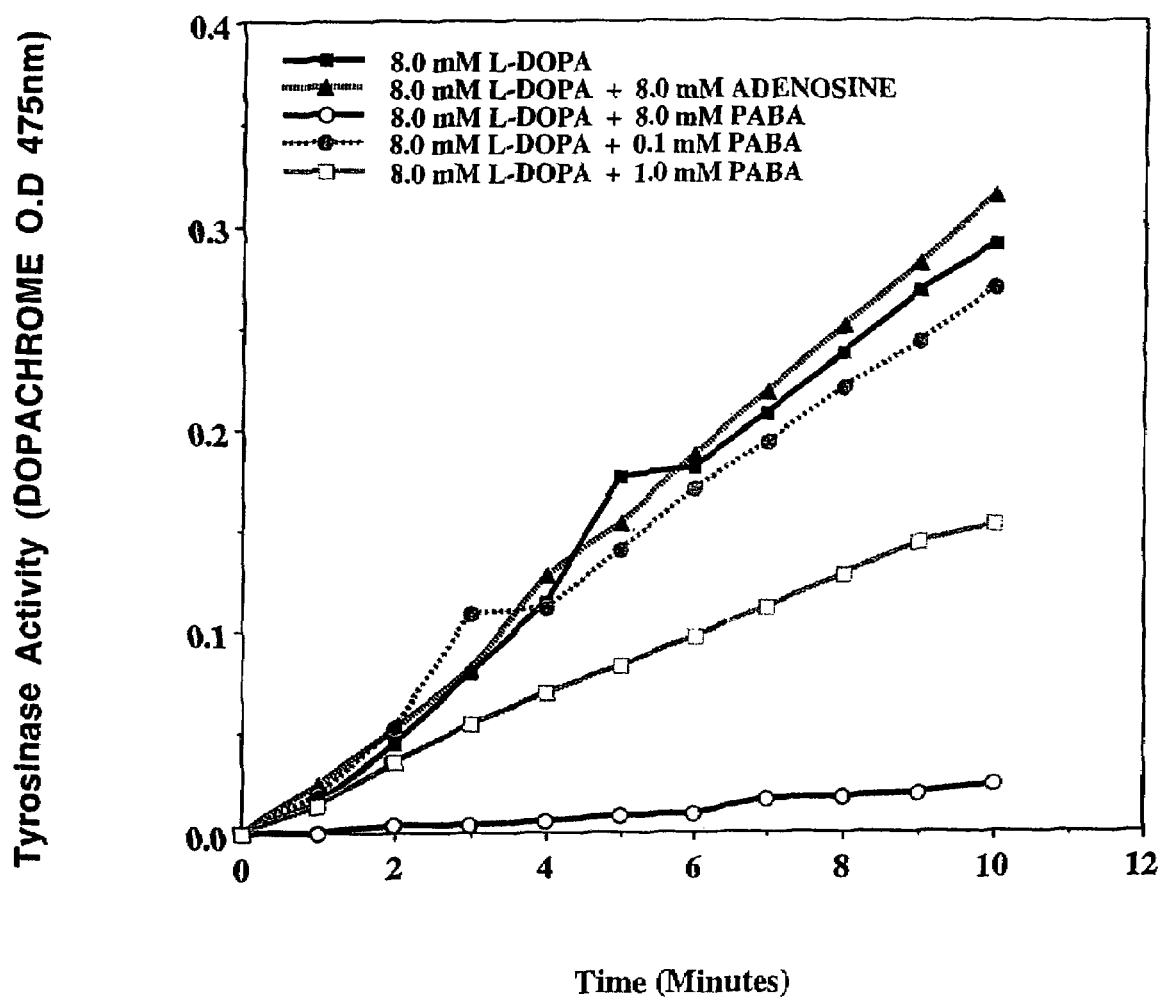
FIG. 2 shows the inhibition of tyrosinase activity by PABA. Tyrosinase activity was assessed by measuring the formation of Dopachrome from L-DOPA using absorbance at 475 nm wavelength.

The present invention relates to methods for the use of PABA to inhibit melanogenesis and to treat melanotic cancer in mammals. In various aspects of the invention, PABA can be administered alone, in combination with one or more chemotherapeutic agents, or in combination with radiation therapy. In one embodiment, PABA is administered in combination with carboplatin and paclitaxel for the treatment of melanoma in a mammal.

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

As used herein, "melanotic cancer" encompasses cancers in which melanin and/or a melanocyte is present. The most common melanotic cancer is melanoma. Other melanotic cancers include, for example, melanotic neuroectodermal tumor of infancy, melanotic malignant peripheral nerve sheath tumor, melanotic medulloblastoma, melanotic neurilemoma, melanotic schwannoma, meningeal melanocytoma, and melanotic ependymoma.

As used herein, an "effective amount" of an agent is an amount sufficient to ameliorate at least one symptom associated with a pathological, abnormal or otherwise undesirable condition, an amount sufficient to prevent or lessen the probability that such a condition will occur or re-occur, or an amount sufficient to delay worsening of such a condition.

As used herein, "melanogenesis" means the process of synthesis of melanin, including, for example, all enzymatic and non-enzymatic reactions related to a chemical precursor of melanin, an intermediate, or a byproduct of the process.

As used herein, the term "inhibit" means to decrease, limit, or block the action or function of a process.

As used herein, the terms "treatment" or "treat" mean the lessening or ameliorating of at least one abnormal or undesirable condition associated with melanotic cancer. Treatment may, for example, cause a reduction in the rate or amount of growth of a melanotic tumor. Treatment also includes reducing or ameliorating the undesirable symptoms of melanotic cancer. The foregoing are merely non-limiting examples of the treatment of melanotic cancer. Other means and outcomes for treating melanotic cancer are also encompassed by the invention.

As used herein, the phrase "a mammal in need of such treatment" refers to a mammal suffering from at least one abnormal or undesirable condition or disorder associated with melanin synthesis or with melanotic cancer.

The phrase "in combination with" refers to a method of treatment in which two or more treatments are administered collectively or according to a specific sequence, such that they produce a desirable effect.

The phrase "pharmaceutically acceptable" refers to molecular entities and compositions that are physiologically tolerable and do not typically produce an allergic or similar toxicity (for example, gastric upset, dizziness and the like) when administered to an individual. Preferably, and particularly where a vaccine is used in humans, the term "pharmaceutically acceptable" may mean approved by a regulatory agency (for example, the U.S. Food and Drug Agency) or listed in a generally recognized pharmacopeia for use in animals (for example, the U.S. Pharmacopeia).

The phrase "recurrent malignant melanoma" means malignant melanoma in which the patient's cancer enlarged in size and/or underwent metastatic spread following completed cancer treatment.

The phrase "non-responsive malignant melanoma" means malignant melanoma in which the patient's cancer enlarged in size and/or underwent metastatic spread during the period of time when cancer treatment was in progress.

PABA is commercially available from, e.g., Sigma-Aldrich Chemical Co., St. Louis, Mo.

The biosynthetic pathway of melanogenesis is a complex process involving the ability of the tyrosinase enzyme to hydroxylate a number of substrates including L-tyrosine and L-DOPA. This process ultimately leads to the formation of melanin. In vitro assays have been developed to measure tyrosinase activity, including measuring the formation of Dopachrome from L-DOPA in the presence of tyrosine. (Heidcamp W (1995) *Cell Biology Lab Manual*, National Science Foundation.) Both L-tyrosine and L-DOPA have chemical structures similar to PABA. It was hypothesized that PABA may be acting as a competitive substrate for tyrosinase, thus inhibiting melanogenesis.

In one aspect of the invention, PABA is used to inhibit melanogenesis in a mammal, preferably a human. Inhibition may be obtained, without limitation, by administration of 10 mg/day to 20 g/day of PABA. Preferably, PABA is administered in amounts of 20 mg/day to 12 g/day.

In another aspect of the invention, PABA is used to treat melanotic cancer in a mammal, preferably a human. Treatment may comprise, without limitation, administration of 10 mg/day to 20 g/day of PABA. Preferably, PABA is administered in amounts of 20 mg/day to 12 g/day.

In another aspect of the invention, an effective amount of PABA is administered in combination with radiation therapy to treat melanoma. Treatment may comprise, without limitation, administration of 10 mg/day to 20 g/day of PABA. Preferably, PABA is administered in amounts of 20 mg/day to 12 g/day. Preferably, radiation is administered in doses of 1 cGy to 100 Gy. More preferably, radiation is administered in doses of 2 cGy to 20 Gy.

In a further aspect of the invention, an effective amount of PABA is administered in combination with one or more chemotherapeutic agents known for use in treating melanoma. Treatment may comprise, without limitation, administration of 10 mg/day to 20 g/day of PABA. Preferably, PABA is administered in amounts of 20 mg/day to 12 g/day. Also preferably, the chemotherapeutic agent is selected from the group including platinum complex, podophyllotoxin, carboplatin, procarbazine, mechlorethamine, cyclophosphamide, camptothecin, ifosfamide, melphalan, chlorambucil, bisulfan, nitrosurea, adriamycin, dactinomycin, daunorubicin HCl, doxorubicin, Doxil (doxorubicin HCl liposome injection), Ellence (epirubicin hydrochloride), bleomycin, plicomycin, mitomycin, etoposide, tamoxifen, paclitaxel (Taxol®), transplatinum, 5-fluorouracil, vincristin, vinblastin, bortezomib (VELCADE™, formerly known as PS-341), dicarbizide, a-interferon (Intron A), Genasense G3139 (Bcl2 antisense oligonucleotide), Gemzar (gencitabine HCl), Xeloda (capecitabine: 5'-deoxy-5-fluoro-N-[(pentyloxy) carbonyl]-cytidine), epithalones A and B, oxaliplatin, inhibitors of the EGFR tyrosine kinase (e.g. OSI-774), C225, Herceptin (trastuzamab), Rituxan (rituximab), Proleukin (aldesleukin), Photofrin (profimer sodium), Ontak (denileukin difitox), Novantrone (mitoxantrone hydrochloride), Nolvadex (tamoxifen citrate), Neupogen (filgrastim), Mylotart (gemtuzumab ozogamicin), Hycamtin (topotecan HCl), Glecvec (imatinib mesylate), Femara (letrozole), Fareston (toremifene citrate), Etopophos (etoposide phosphate), Ethyol (amifostine), Camptosar (irinotecan HCl), Campath (alemtuzumab), Busulfex (busulfan), Blenoxane (bleomycin sulfate), Aromasin (exemestane), Arimidex (anastrozole), Taxotere (docetaxel), Temodar (temozolomide), and Trisenox (arsenic trioxide).

More preferably, the one or more chemotherapeutic agents selected are paclitaxel (Taxol®, available from Bristol-Meyers Squibb Co., Princeton, N.J.) and/or docetaxel (Taxotere®, available from Aventis Pharmaceuticals, Inc., Bridgewater, N.J.). Paclitaxel stabilizes mictotubules through the binding of tubulin, which results in arrest of mitosis. In accordance with the invention, paclitaxel is administered in standard doses well known to those skilled in the art. Docetaxel binds free microtubules and results in arrest of mitosis. In accordance with the invention, docetaxel is administered in standard doses well known to those skilled in the art.

Carboplatin (Paraplatin®, available from Bristol-Meyers Squibb Co., Princeton, N.J.) is a platinum coordination compound that produces cell cycle non-specific interstrand DNA cross-links. In accordance with the invention, carboplatin is administered in standard doses well known to those skilled in the art. (See also Physician's Desk Reference, $57^{th}$ ed. 2003.) One method of dosing carboplatin according to the invention includes a dose calculation to meet a target area under the curve (AUC) of concentration multiplied by time according to the Calvert formula using an estimated glomerular filtration rate (GFR) derived from the Jelliffe formula. The Calvert formula is: total dose (mg)=(target AUC)×(GFR+25). For the purposes of this dosing method, GFR is considered the equivalent to creatinine clearance. Creatinine clearance (Ccr) is estimated by the Jelliffe formula: Ccr (ml/min)={98−[0.8 (age−20)]}÷Scr; where age=patient's age in years from 20-80 and Scr=serum creatinine in mg/dl. For patients younger than 20, 20 is substituted for the patient's actual age. For patients older than 80, 80 is substituted for the patient's actual age.

In a preferred embodiment, PABA is administered in combination with carboplatin and paclitaxel. In one embodiment, PABA is administered at a dose of 2 grams orally for 5 days prior to the administration of carboplatin and is continued daily for a total of 10 days. Carboplatin is administered on the sixth day of PABA administration at a dose according to the Calvert formula with a target AUC of 5 milligram/milliliter*minute. Paclitaxel is administered at a dose of 100 milligrams/meter$^2$ intravenously on the sixth day of PABA treatment. A treatment cycle begins on the first day of PABA treatment and lasts 21 days. The interval between treatment cycles is 11 days unless dose limiting toxicity ("DLT") occurs. Dose limiting toxicity includes, for example, hematologic toxicity, nausea/vomiting, mucositis, arthralgias and myalgias. peripheral neuropathy, and liver function test abnormalities.

In another embodiment according to the invention, the combination of PABA, carboplatin, and paclitaxel is administered in a regimen that includes escalating doses of paclitaxel. In one such embodiment, treatment is initiated with PABA at a dose of 2 grams orally for 5 days prior to the administration of carboplatin and is continued daily for a total of 10 days. Carboplatin is administered on the sixth day of PABA administration at a dose calculated according to the Calvert formula with a target AUC of 5 milligram/milliliter*minute. A treatment cycle lasts 21 days and begins on the first day of PABA treatment. Following a treatment cycle, and in the absence of DLT, a second cycle is initiated with the administration of PABA at a dose of 2 grams orally for 5 days prior to the administration of carboplatin and is continued daily for a total of 10 days. Carboplatin is administered on the sixth day of PABA administration at a dose calculated according to the Calvert formula with a target AUC of 5 milligram/milliliter*minute. Paclitaxel is administered at a dose of 100 milligrams/meter$^2$ intravenously on the sixth day of PABA administration. If the patient tolerates this treatment cycle without DLT, a third treatment cycle is initiated 11 days later with the administration of PABA at a dose of 2 grams orally for 5 days prior to the administration of carboplatin and is continued daily for a total of 10 days. Carboplatin is administered on the sixth day of PABA at a dose calculated according to the Calvert formula with a target AUC of 5 milligram/milliliter*minute. Paclitaxel is administered at a dose of 125 milligrams/meter$^2$ intravenously on the sixth day of PABA treatment. If the patient tolerates this treatment cycle without DLT, a fourth treatment cycle is initiated 11 days later with the administration of PABA at a dose of 2 grams orally for 5 days prior to the administration of carboplatin and is continued daily for a total of 10 days. Carboplatin is administered on the sixth day of PABA treatment at a dose calculated according to the Calvert formula with a target AUC of 5 milligram/milliliter*minute. Paclitaxel is administered at a dose of 150 milligrams/meter$^2$ intravenously on the sixth day of PABA treatment. If the patient tolerates this treatment cycle without DLT, a fifth treatment cycle is initiated 11 days later with the administration of PABA at a dose of 2 grams orally for 5 days prior to the administration of carboplatin and is continued daily for a total of 10 days. Carboplatin is administered on the sixth day of PABA administration at a dose calculated according to the Calvert formula with a target AUC of 5 milligram/milliliter*minute. Paclitaxel is started at a dose of 175 milligrams/meter$^2$ intravenously on the sixth day of PABA administration.

Pharmaceutical Compositions

For administration to patients according to the method of the present invention, PABA may be formulated into a pharmaceutical composition. The pharmaceutical composition may include additives, such as a pharmaceutically acceptable carrier or diluent, a flavorant, a sweetener, a preservative, a dye, a binder, a suspending agent, a dispersing agent, a colorant, a disintegrant, an excipient, a film forming agent, a lubricant, a plasticizer, an edible oil or any combination of two or more of the foregoing.

Suitable pharmaceutically acceptable carriers or diluents include, but are not limited to, ethanol; water; glycerol; propylene glycol, aloe vera gel; allantoin; glycerin; vitamin A and E oils; mineral oil; PPG2 myristyl propionate; magnesium carbonate; potassium phosphate; vegetable oil; animal oil; and solketal.

Suitable binders include, but are not limited to, starch; gelatin; natural sugars, such as glucose, sucrose and lactose; corn sweeteners; natural and synthetic gums, such as acacia, tragacanth, vegetable gum, and sodium alginate; carboxymethylcellulose; hydroxypropylmethylcellulose; polyethylene glycol; povidone; waxes; and the like.

Suitable disintegrants include, but are not limited to, starch, e.g., corn starch, methyl cellulose, agar, bentonite, xanthan gum, sodium starch glycolate, crosspovidone and the like.

Suitable lubricants include, but are not limited to, sodium oleate, sodium stearate, sodium stearyl fumarate, magnesium stearate, sodium benzoate, sodium acetate, sodium chloride and the like.

A suitable suspending agent is, but is not limited to, bentonite, ethoxylated isostearyl alcohols, polyoxyethylene sorbitol and sorbitan esters, microcrystalline cellulose, aluminum metahydroxide, agar-agar and tragacanth, or mixtures of two or more of these substances, and the like.

Suitable dispersing and suspending agents include, but are not limited to, synthetic and natural gums, such as vegetable gum, tragacanth, acacia, alginate, dextran, sodium carboxymethylcellulose, methylcellulose, polyvinyl-pyrrolidone and gelatin.

Suitable film forming agents include, but are not limited to, hydroxypropylmethylcellulose, ethylcellulose and polymethacrylates.

Suitable plasticizers include, but are not limited to, polyethylene glycols of different molecular weights (e.g., 200-8000 Da) and propylene glycol.

Suitable colorants include, but are not limited to, ferric oxide(s), titanium dioxide and natural and synthetic lakes.

Suitable edible oils include, but are not limited to, cottonseed oil, sesame oil, coconut oil and peanut oil.

Examples of additional additives include, but are not limited to, sorbitol, talc, stearic acid, dicalcium phosphate and polydextrose.

Unit Dosage Forms

The pharmaceutical composition may be formulated as unit dosage forms, such as tablets, pills, hard or soft shell capsules, caplets, boluses, powders, granules, sterile parenteral solutions, sterile parenteral suspensions, sterile parenteral emulsions, elixirs, tinctures, metered aerosol or liquid sprays, drops, ampoules, autoinjector devices or suppositories. Unit dosage forms may be used for oral, parenteral, intranasal, sublingual or rectal administration, or for administration by inhalation or insufflation, transdermal patches, and a lyophilized composition. In general, any delivery of active ingredients that results in systemic availability of such ingredients can be used in practicing the present invention. Preferably the unit dosage form is an oral dosage form, most preferably a solid oral dosage form, therefore the preferred dosage forms are tablets, pills, caplets and capsules. Parenteral preparations (e.g., injectable preparations in saline and preparations for powder jet systems) comprise another embodiment of the invention.

Solid unit dosage forms may be prepared by mixing an active agent of the present invention with a pharmaceutically acceptable carrier and any other desired additives as described above. The mixture is typically mixed until a homogeneous mixture of the active agents of the present invention, the carrier and any other desired additives is formed, i.e., until the active agent is dispersed evenly throughout the composition. In this case, the compositions can be formed as dry or moist granules.

Dosage forms with predetermined amounts of PABA may be formulated starting with compositions with known quantities of PABA using methods well known in the art. In a preferred embodiment a dosage form is obtained by mixing compositions comprising known quantities of PABA.

Dosage forms can be formulated as, for example, "immediate release" dosage forms. "Immediate release" dosage forms are typically formulated as tablets that release at least 70%-90% of the active ingredient within 30-60 min when tested in a drug dissolution test, e.g., U.S. Pharmacopeia standard <711>. In a preferred embodiment, immediate dosage forms release 75% of the active ingredients in 45 min.

Dosage forms can also be formulated as, for example, "controlled release" dosage forms. "Controlled," "sustained," "extended" or "time release" dosage forms are equivalent terms that describe the type of active agent delivery that occurs when the active agent is released from a delivery vehicle at an ascertainable and modifiable rate over a period of time, which is generally on the order of minutes, hours or days, typically ranging from about sixty minutes to about 3 days, rather than being dispersed immediately upon entry into the digestive tract or upon contact with gastric fluid. A controlled release rate can vary as a function of a multiplicity of factors. Factors influencing the rate of delivery in controlled release include the particle size, composition, porosity, charge structure, and degree of hydration of the delivery vehicle and the active ingredient(s), the acidity of the environment (either internal or external to the delivery vehicle), and the solubility of the active agent in the physiological environment, i.e., the particular location along the digestive tract. Typical parameters for dissolution test of controlled release forms are found in U.S. Pharmacopeia standard <724>.

Dosage forms can also be formulated to deliver active agent in multiphasic stages whereby a first fraction of an active ingredient is released at a first rate and at least a second fraction of active ingredient is released at a second rate. In a preferred embodiment, a dosage form can be formulated to deliver active agent in a biphasic manner, comprising a first "immediate release phase", wherein a fraction of active ingredient is delivered at a rate set forth above for immediate release dosage forms, and a second "controlled release phase," wherein the remainder of the active ingredient is released in a controlled release manner, as set forth above for controlled release dosage forms.

Tablets or pills can be coated or otherwise compounded to form a unit dosage form which has delayed and/or prolonged action, such as time release and controlled release unit dosage forms. For example, the tablet or pill can comprise an inner dosage and an outer dosage component, the latter being in the form of a layer or envelope over the former. The two components can be separated by an enteric layer which serves to resist disintegration in the stomach and permits the inner component to pass intact into the duodenum or to be delayed in release.

Biodegradable polymers for controlling the release of the active agents, include, but are not limited to, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

For liquid dosage forms, the active substances or their physiologically acceptable salts are brought into solution, suspension or emulsion, optionally with the usually employed substances such as solubilizers, emulsifiers or other auxiliaries. Solvents for the active combinations and the corresponding physiologically acceptable salts, can include water, physiological salt solutions or alcohols, e.g. ethanol, propane-diol or glycerol. Additionally, sugar solutions such as glucose or mannitol solutions may be used. A mixture of the various solvents mentioned may further be used in the present invention.

A transdermal dosage form also is contemplated by the present invention. Transdermal forms may be a diffusion-driven transdermal system (transdermal patch) using either a fluid reservoir or a drug-in-adhesive matrix system. Other transdermal dosage forms include, but are not limited to, topical gels, lotions, ointments, transmucosal systems and devices, and iontohoretic (electrical diffusion) delivery system. Transdermal dosage forms may be used for timed release and controlled release of the active agents of the present invention.

Pharmaceutical compositions and unit dosage forms of the present invention for administration parenterally, and in particular by injection, typically include a pharmaceutically acceptable carrier, as described above. A preferred liquid carrier is vegetable oil. Examples of solid carriers are lactose, terra alba, sucrose, cyclodextrin, talc, agar, pectin, acacia, stearic acid and lower alkyl ethers of cellulose corn starch, potato starch, talcum, magnesium stearate, gelatine, lactose, gums, and the like. Injection may be, for example, intratumoral, intravenous, intrathecal, intramuscular, intratracheal, or subcutaneous. Intravenous injection is preferred.

The active agent also can be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The pharmaceutical compositions of the present invention also may be coupled with soluble polymers as targetable drug carriers. Such polymers include, but are not limited to, polyvinyl-pyrrolidone, pyran copolymer, polyhydroxypropylmethacryl -amidephenol, polyhydroxy-ethylaspartamidephenol, and polyethyl-eneoxideopolylysine substituted with palmitoyl residues.

Administration

The pharmaceutical composition or unit dosage forms of the present invention may be administered by a variety of routes such as intravenous, intratracheal, subcutaneous, oral, intratumoral, mucosal parenteral, buccal, sublingual, ophthalmic, pulmonary, transmucosal, transdermal, and intramuscular. Unit dosage forms also can be administered in intranasal form via topical use of suitable intranasal vehicles, or via transdermal routes, using those forms of transdermal skin patches known to those of ordinary skill in the art. Oral administration is preferred. Also preferred is administration by local intratumoral injection.

The pharmaceutical composition or unit dosage forms of the present invention may be administered to a mammal, preferably a human being, in need of cancer treatment. The pharmaceutical composition or unit dosage form of the present invention may be administered according to a dosage and administration regimen defined by routine testing in light of the guidelines given above in order to obtain optimal activity while minimizing toxicity or side-effects for a particular patient. However, such fine turning of the therapeutic regimen is routine in light of the guidelines disclosed in this specification.

The dosage of the composition of the present invention may vary according to a variety of factors such as the underlying disease state, the individual's condition, weight, sex and age and the mode of administration. For oral administration, the pharmaceutical compositions can be provided in the form of scored or unscored solid unit dosage forms.

The pharmaceutical composition or unit dosage form may be administered in a single daily dose, or the total daily dosage may be administered in a plurality of divided doses. In addition, co-administration or sequential administration of other active agents may be desirable. The pharmaceutical composition of the invention may be combined with any known drug therapy, preferably for the treatment of cancer.

For combination therapy, the pharmaceutical PABA composition of the present invention and the other active agent(s) (e.g., chemotherapeutic agent(s)) may initially be provided as separate dosage forms until an optimum dosage combination and administration regimen is achieved. Therefore, the patient may be titrated to the appropriate dosages for his/her particular condition. After the appropriate dosage of each of the compounds is determined to achieve the desired effect without untoward side effects, the patient then may be switched to a single dosage form containing the appropriate dosages of the pharmaceutical PABA composition and the other active agent(s), or may continue with a dual (or multi) dosage form.

The exact dosage and administration regimen utilizing the combination therapy of the present invention is selected in accordance with a variety of factors including type, species, age, weight, sex and medical condition of the patient; the route of administration; the renal and hepatic function of the patient; the treatment history of the patient; and the responsiveness of the patient. Optimal precision in achieving concentrations of compounds within the range that yields efficacy without toxicity requires a regimen based on the kinetics of the drug's availability to target sites. This involves a consideration of the absorption, distribution, metabolism, excretion of a drug, and responsiveness of the patient to the dosage regimen. However, such fine tuning of the therapeutic regimen is routine in light of the guidelines disclosed in this specification.

EXAMPLES

Example 1

PABA Suppresses Secretion of Melanin in B16 Melanoma Cells Cultured in Vitro

Growth of melanotic B16 melanoma cells (Engbring J A et al. (2002) *Cancer Res* 62:3549-3554) in DMEM medium (available from, e.g. Life Technologies, Inc., Rockville Md.) resulted in a change of the color of the medium from red to brown due to the accumulation of secreted melanin. Growth of melanotic B16 melanoma cells in RPMI medium (available from, e.g. Life Technologies, Inc., Rockville Md.) did not result in a color change. The RPMI medium remained red due to the inhibition of melanin secretion. One of the major components in RPMI that is absent in DMEM is PABA. To assess the effect of PABA on melanin secretion from B16 cells, PABA was added to DMEM culture medium to achieve the same concentration as that found in the RPMI medium: 0.1 mg of PABA per milliliter of medium. Cells were grown in PABA-supplemented DMEM medium for seven days. The PABA-supplemented medium remained red, while the unsupplemented medium turned brown. These results suggest that PABA inhibits the formation and/or secretion of melanin.

Example 2

Time and Concentration Dependent Inhibition of Melanin Synthesis and Secretion

To further analyze the effects of PABA on B16 melanoma cell melanin secretion, PABA was added at concentrations of 0.5 mg/day and 1.0 mg/day to B16 melanoma cells cultured in DMEM. Samples of the culture medium were then analyzed for melanin content by measuring absorbance at wavelengths of 405 nm and 660 nm. (Kowalczuk C et al. (2001) *Inter J Rad Biol* 77:883-890.) The addition of PABA caused a time dependent and concentration dependent inhibition of melanin secretion (FIGS. 1A and 1B).

Example 3

PABA Suppresses Intracellular Synthesis of Melanin within B16 Melanoma Cells

To determine whether PABA inhibits the intracellular synthesis of melanin in B16 cells, cells were grown in DMEM in the presence or absence of 0.1 mg/ml PABA. Following three weeks of culture, cells were collected by centrifugation. Cell pellets from cells cultured in the absence of PABA appeared black, as normal, indicating the presence of melanin. B16 melanoma cells cultured in the presence of PABA appeared much lighter in color, indicating a reduction in melanin accumulation. These results indicate that PABA inhibits melanin synthesis and/or accumulation within melanoma cells.

Example 4

PABA Inhibits Tyrosinase Activity Dose Dependently

The reduction in cell-associated melanin observed in cells treated with PABA suggested that PABA inhibits a step in the biosynthetic pathway of melanin synthesis. The effects of PABA on tyrosinase activity were evaluated by measuring the formation of Dopachrome using a previously published method. (Heidcamp W (1995), supra.) L-DOPA (8.0 mM) was resuspended in sodium citrate buffer and 800 U of purified tyrosinase was added. Tyrosinase activity was measured by monitoring the formation of Dopachrome by measuring the optical density of the mixture at a wavelength of 475 nm. To assess the effects of PABA, the reactions were performed in the presence or absence of PABA. As a control, reactions were performed in the presence of adenosine instead of PABA. Results are shown in FIG. 2. Addition of PABA led to a dose dependent inhibition of Dopachrome formation. These results indicate that PABA is a potent inhibitor of tyrosinase and suggests that inhibition of tyrosinase is the mechanism by which PABA inhibits melanin accumulation in cells.

Example 5

PABA Inhibits B16 Melanoma Metastasis in the Chick Embryo Model

Figure 3:
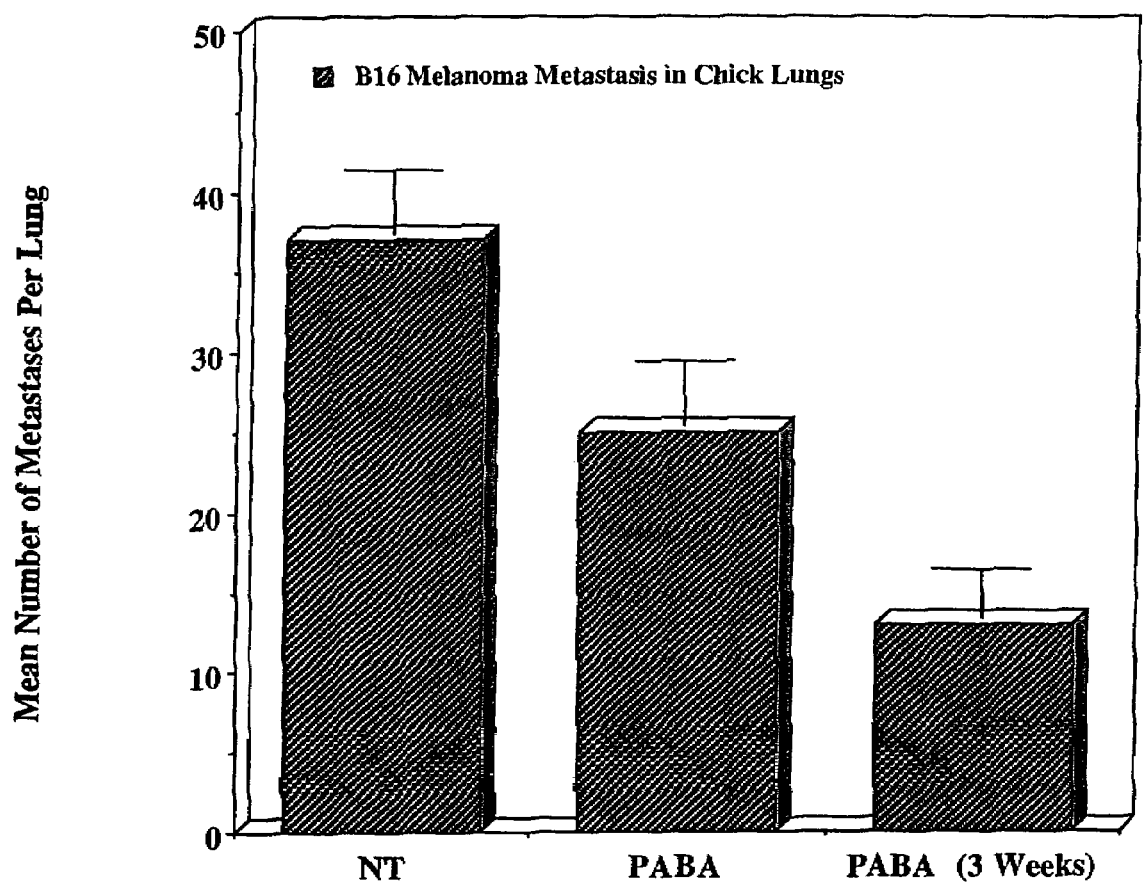
FIG. 3 shows the effect of PABA on B16 melanoma metastasis in chick lungs. The number of melanoma metastases were measured by counting the number of metastatic lung tumor lesions present in lungs from sacrificed chick embryos.

The effect of PABA on the aggressiveness and invasiveness of B16 melanoma was measured in a chick embryo model. (Brooks PC et al. (1994) *Cell* 79:1157-1164.) The effects of PABA on B16 experimental metastasis in vivo were evaluated to determine the role melanin synthesis plays in the aggressiveness and invasiveness of melanoma metastasis. B16 melanoma cells grown in the presence or absence of 0.1 mg/ml PABA for one to three weeks were injected into 12-day old chick embryos. At the end of a 7-day incubation period, the embryos were sacrificed and the number of metastatic lung tumor lesions were quantified. A time dependent inhibition of B16 melanoma metastasis was observed for B16 melanoma cells grown in the presence of PABA (FIG. 3). These results indicate that PABA inhibits the growth of non-primary melanomas in vivo.

Example 6

Effect of PABA on B16 Melanoma Tumor Growth in the Chick Embryo

Figure 4:
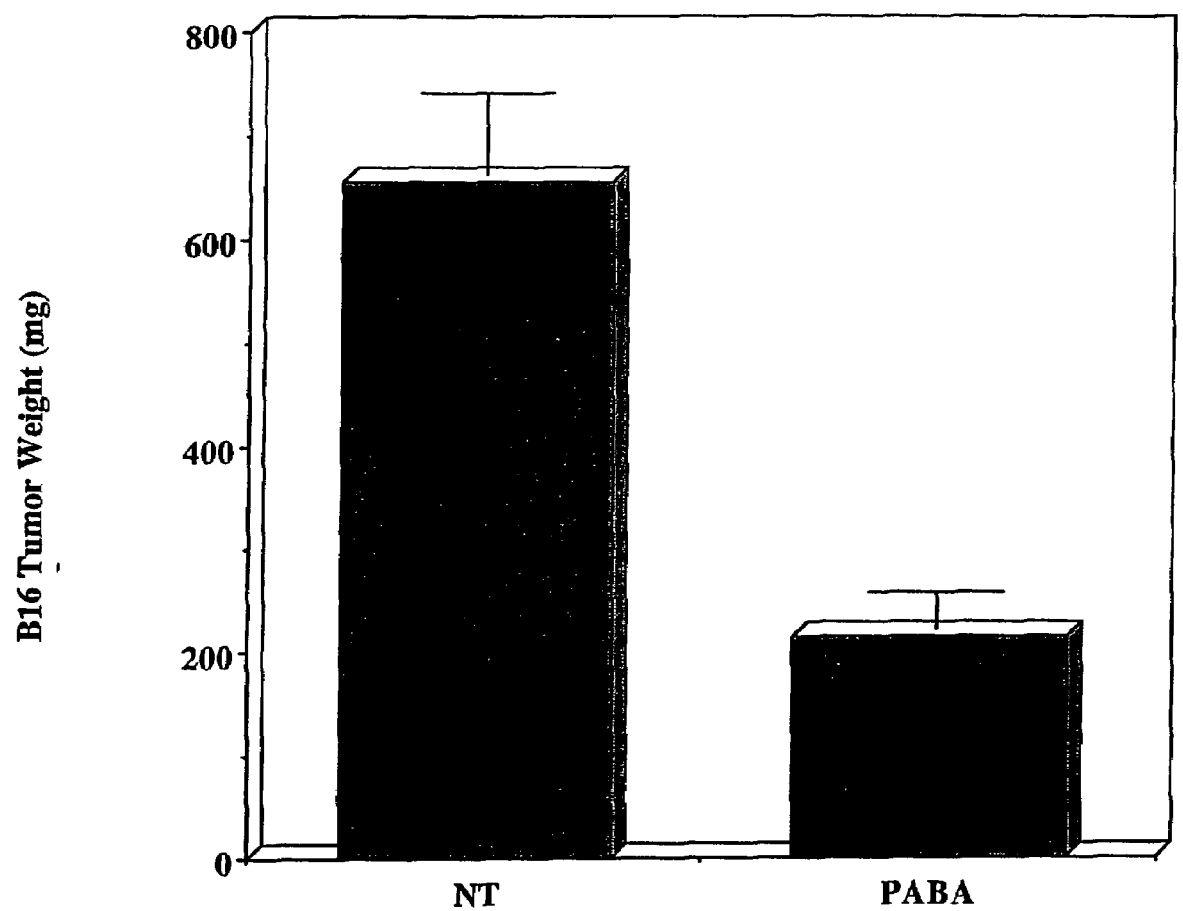
FIG. 4 shows the effect of PABA on B16 melanoma tumor growth.

The effect of PABA on solid tumor growth in vivo were evaluated using the chick embryo tumor growth assay. (Petitclerc E et al. (2000) *J Biol Chem* 275:8051-8061.) B16 melanoma cells were grown in the presence or absence of 0.1 mg/ml PABA for 6 weeks. Cells were harvested and $2.5 \times 10^5$ cells from each group were inoculated in the chorioallantoic membranes (CAM) of 10-day old chick embryos. The embryos were allowed to develop for a further seven days. At the end of the 7-day incubation period, the embryos were sacrificed and the tumors removed and wet weights determined. Tumors formed from B16 melanoma cells treated with PABA were, on average, 60% smaller than tumors derived from untreated B16 melanoma cells (FIG. 4). These results indicate that treatment of B16 melanoma cells with PABA inhibits tumor growth in vivo.

Example 7

PABA Enhances the Anti-Proliferative Effects of Radiation on B16 Melanoma Cells

Figure 5:
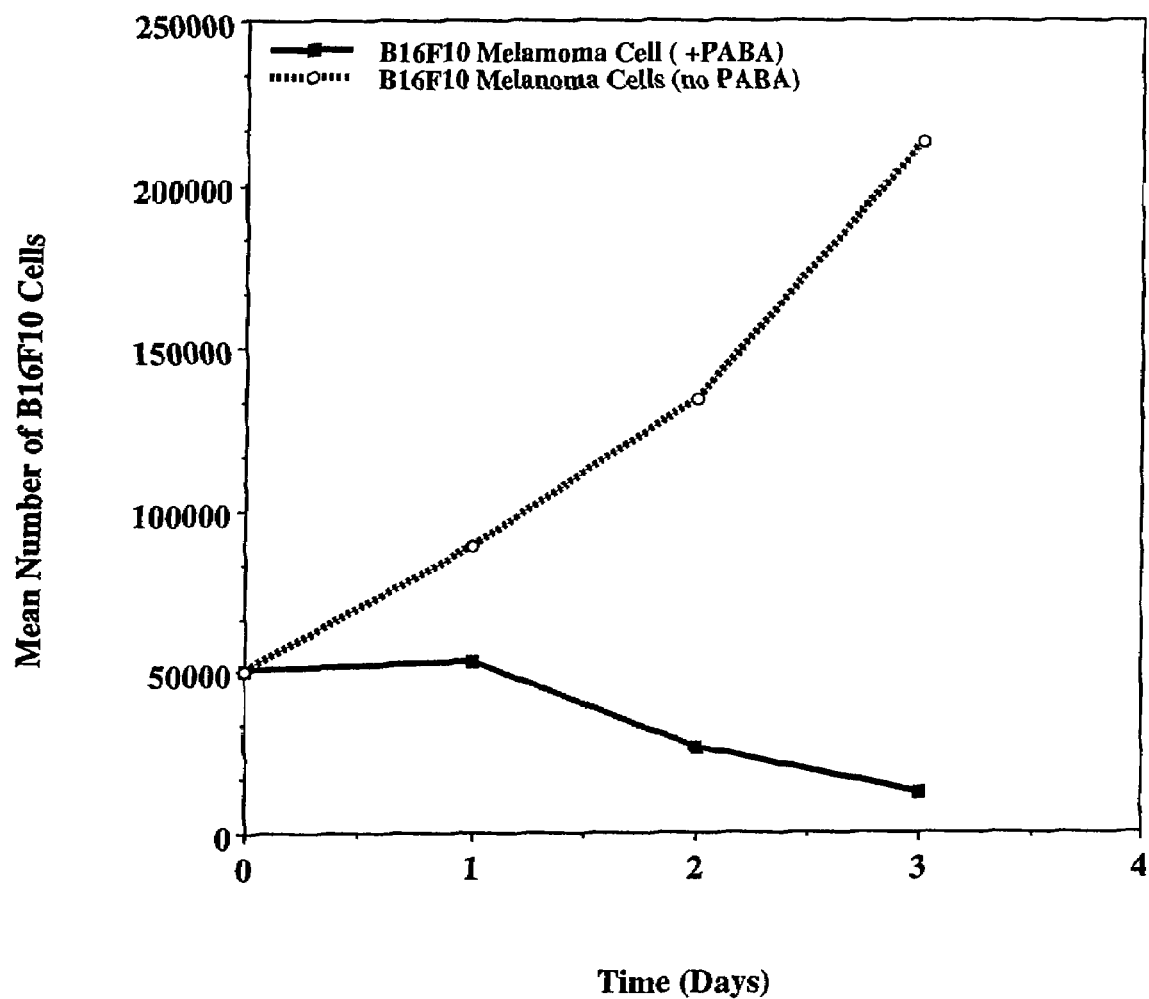
FIG. 5 shows the effect of PABA and 10 Gy of ionizing radiation on B16 melanoma cell proliferation. Cell proliferation was determined by direct cell counts.

Previous studies have suggested that the amount of intracellular melanin present in a melanoma cell is inversely related to the radiosensitivity of that cell. (Kinnaert E et al. (2000) *Radiation Res* 154:497-502.) Thus, blocking melanin synthesis or melanogenesis may cause melanoma cells to become much more sensitive to radiation therapy. To test the effect of PABA on the anti-proliferative effects of ionizing radiation, B16 melanoma cells grown in the presence or absence of 0.1 mg/ml PABA were treated with a single fraction dose of 10 Gy of ionizing radiation. Cell proliferation was monitored by direct cell counts over a 3-day incubation period. Results showed that PABA treatment increased the anti-proliferative and cytotoxic effects of a single fraction dose of radiation, compared with cells not receiving PABA (FIG. 5).

Example 8

Figure 6:
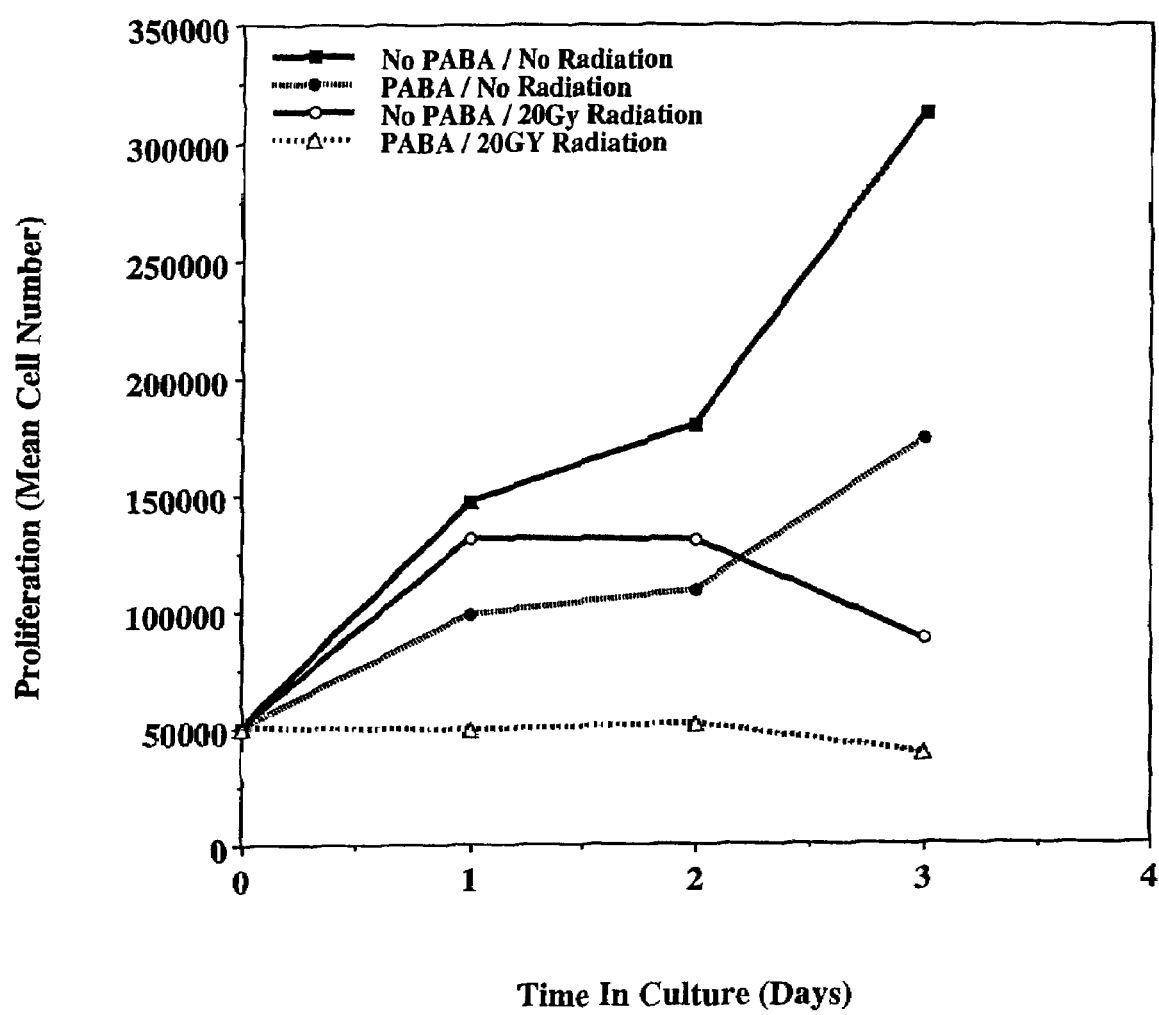
FIG. 6 shows the effect of PABA and 20 Gy of ionizing radiation on human 1424 melanoma cell proliferation. Cell proliferation was determined by direct cell counts.

PABA Enhances the Anti-Proliferative Effects of Radiation on Human 1424 Melanoma Cells The radiation-enhancing effect of PABA on melanoma observed in B16 melanoma cells was confirmed in the pigmented human melanoma cell line G-361 (ATCC Number CRL-1424, (1978) *Pediatr Res* 12:485.) The human G-361 melanoma cells are more resistant to radiation than B16 melanoma cells and thus require a higher dose of ionizing radiation to inhibit growth, compared with B16 cells. Human G-361 melanoma cells were treated with 20 Gy of radiation, either alone or in combination with 0.1 mg/ml PABA, as described in example 7. A single dose of ionizing radiation significantly inhibited the proliferation of human G-361 melanoma cells (FIG. 6). In comparison, the combination of PABA and radiation essentially completely inhibited the proliferation of human G-361 melanoma cells (FIG. 6). These results confirm that the combination of PABA and radiation has enhanced anti-proliferative effects, compared to radiation alone.

Example 9

PABA Enhances the Anti-Proliferative Effects of Taxol on B16 Melanoma Cells

Figure 7:
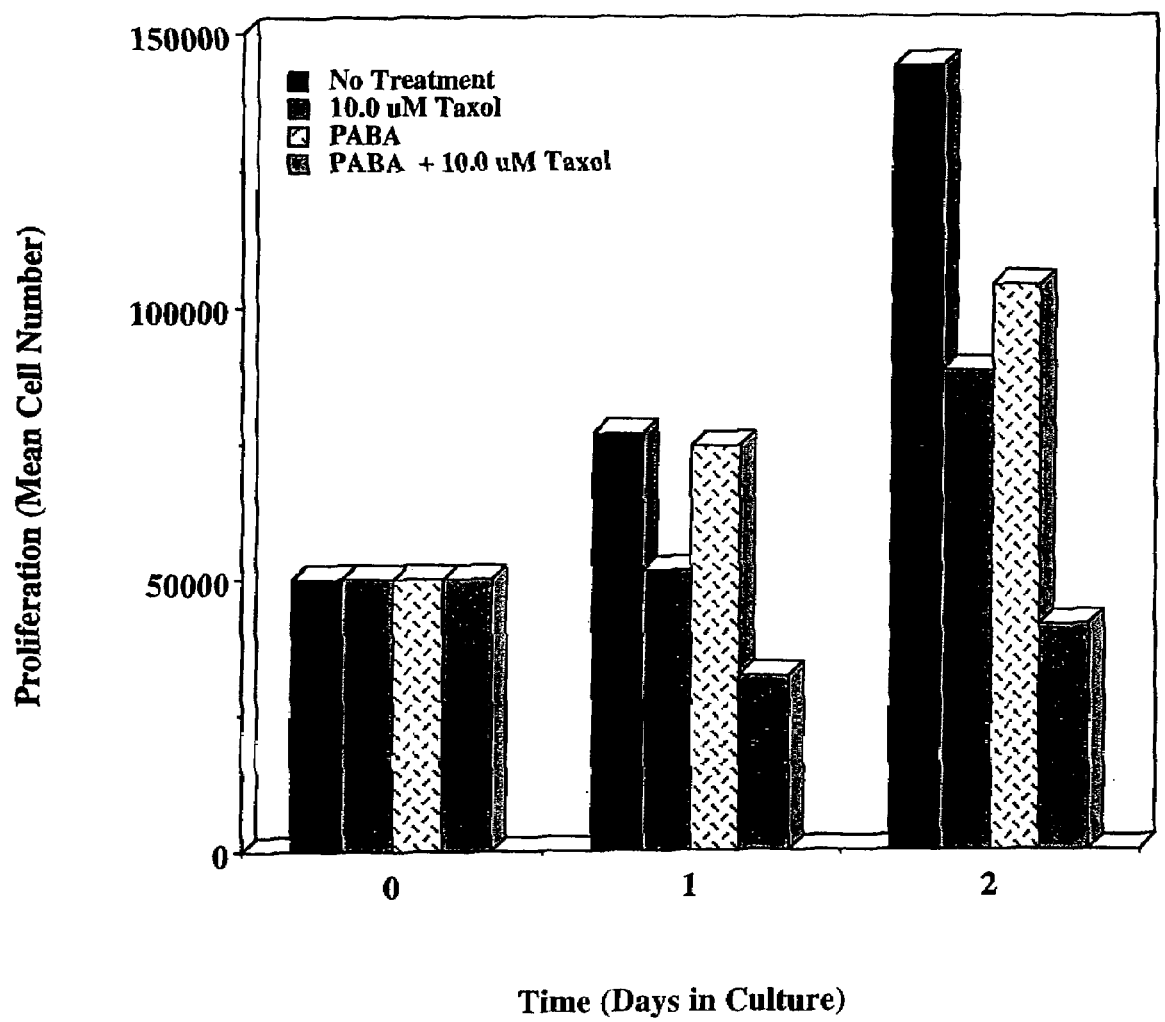
FIG. 7 shows the effect of PABA and Taxol on B16 melanoma cell proliferation. Cell proliferation was determined by direct cell counts.

The ability of PABA to enhance the anti-proliferative effect of the chemotherapeutic agent, Taxol, was tested in B16 melanoma cells. Cells were grown in DMEM medium in the presence or absence of 0.1 mg/ml PABA and/or 10.0 µM paclitaxel (Taxol). Cell proliferation was monitored by direct cell counts over a 48-hour incubation period. Paclitaxel significantly inhibited B16 melanoma cell proliferation, as compared to no treatment (FIG. 7). Combined treatments of PABA and Taxol showed an enhanced anti-proliferative effect on cells, compared to Taxol alone (FIG. 7). These results indicate that PABA enhances the anti-tumor activity of Taxol.

Example 10

Effect of PABA on the Proliferation of Lewis Lung Carcinoma Cells

Figure 8:
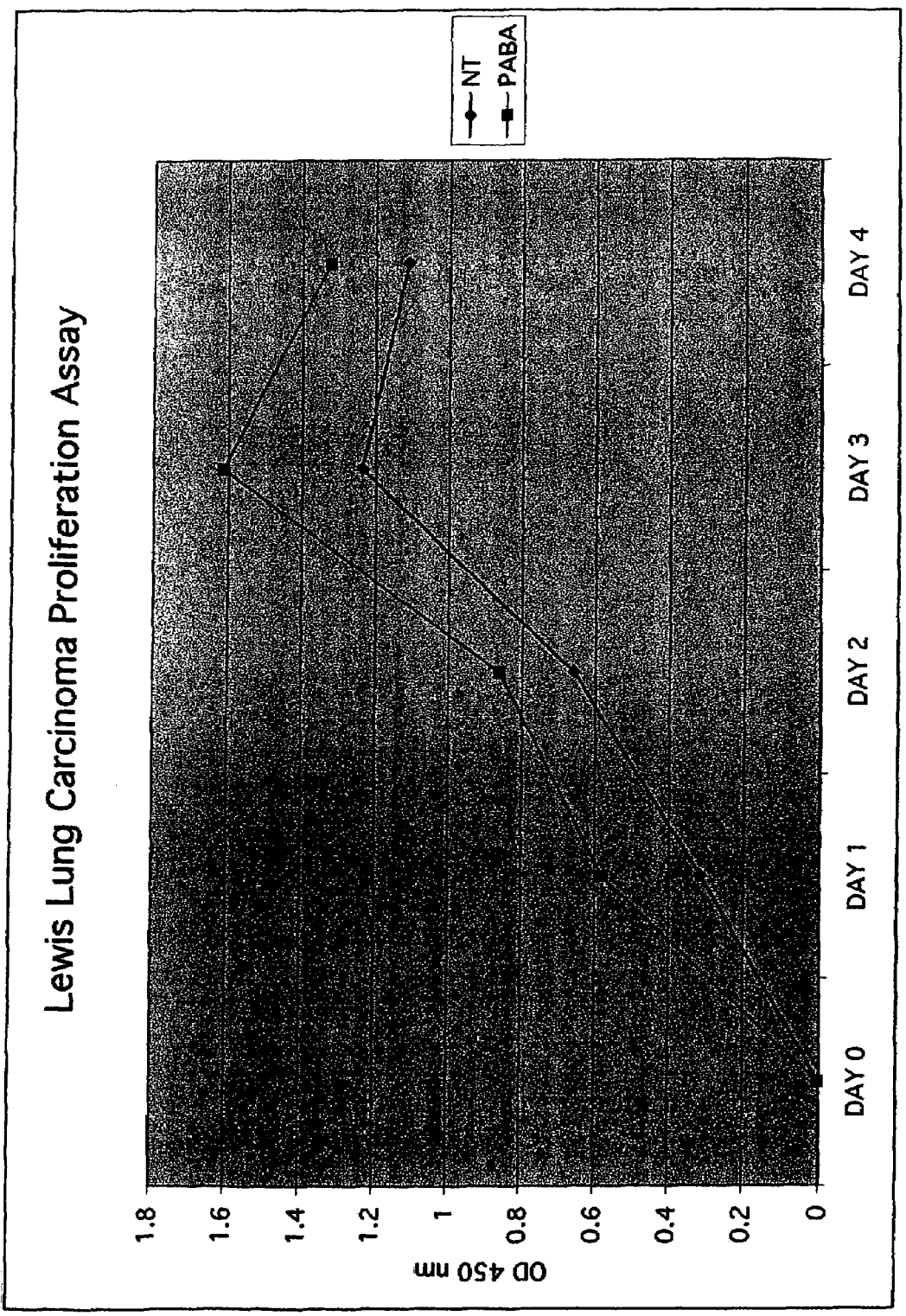
FIG. 8 shows the effect of PABA on Lewis Lung Carcinoma cell proliferation.

The anti-proliferative effect of PABA on carcinoma cells was tested on Lewis Lung Carcinoma (LLC) cells. (Young M R et al. (2003) *Int J Cancer* 103:38-44.) Cells were grown in DMEM medium in the presence or absence of 0.1 mg/ml PABA. Cell proliferation was monitored by direct cell counts over a 48-hour incubation period. The addition of PABA increased the proliferation of LLC cells (FIG. 8). In contrast to the effect of PABA on melanoma cells, these results indicate that PABA enhances, rather than inhibits, the proliferation of carcinoma cells.

Example 11

Effect of PABA on Lewis Lung Carcinoma Tumor Growth

Figure 9:
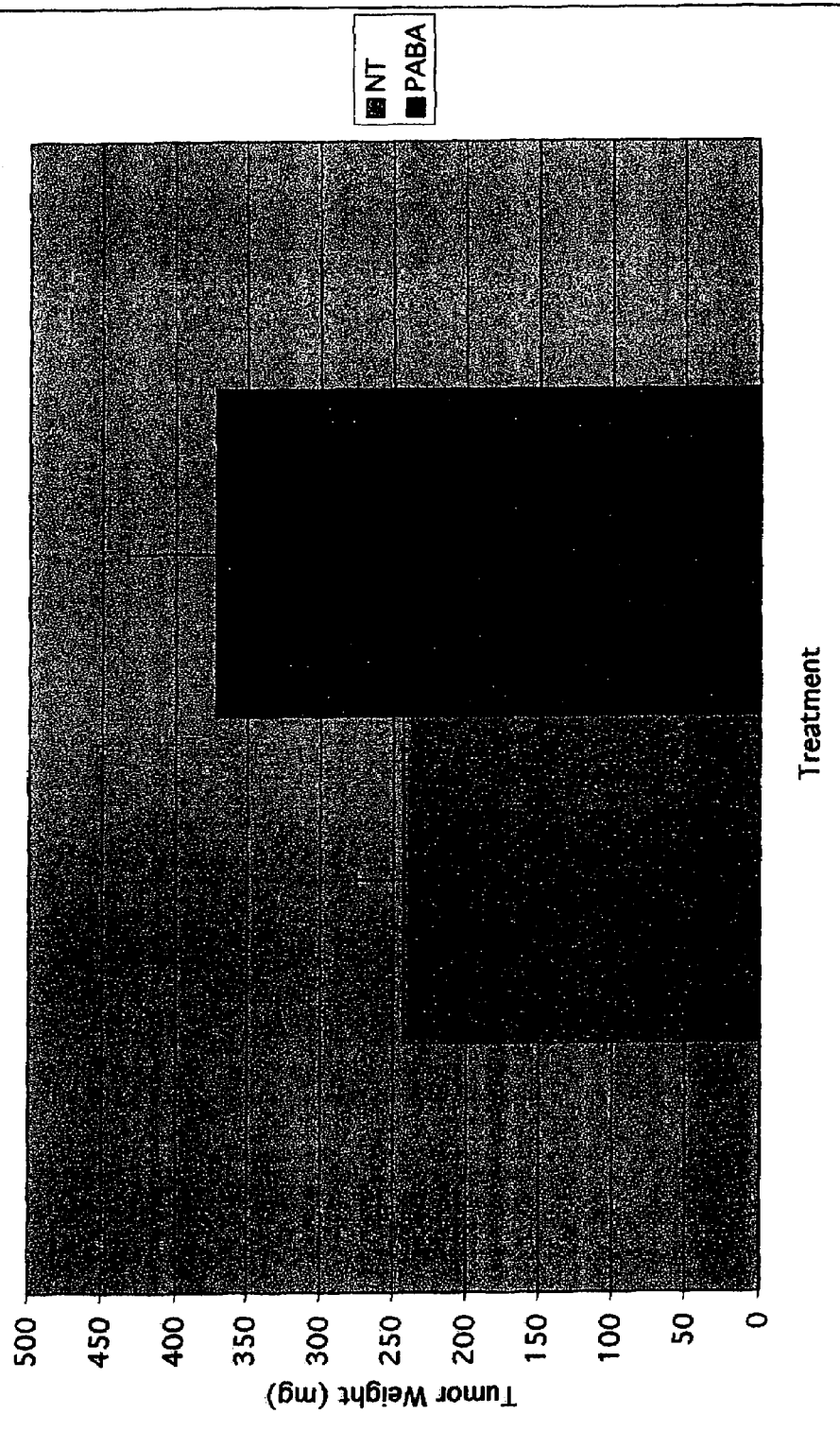
FIG. 9 shows the effect of PABA on Lewis Lung Carcinoma tumor growth.

The effect of PABA on the growth of carcinoma tumors was tested using the Lewis Lung Carcinoma (LLC) tumor growth assay. (Mauceri H J et al. (2002) *Cancer Chemother Pharmacol* 50:412-418.) LLC cells were grown in DMEM medium in the presence or absence of 0.1 mg/ml PABA for 3 weeks. Cells were harvested and $2 \times 10^6$ cells from each group were inoculated in the CAMs of 10-day old chick embryos. The embryos were allowed to develop for a further seven days. At the end of the 7-day incubation period, the embryos were sacrificed and the tumors removed and wet weights determined. Tumors formed from LLC cells treated with PABA were, on average, significantly larger than tumors derived from untreated LLC cells (FIG. 9). In contrast to the effect of PABA on melanoma tumors, these results indicate that treatment of LLC cells with PABA enhances, rather than inhibits, carcinoma tumor growth.

Example 12

In Vivo Effects of PABA on the Treatment of Melanoma with Ionizing Radiation

The chick embryo tumor growth assay (Petitclerc E et al. (2000) *J Biol Chem* 275:8051-8061) was used to determine whether PABA enhances the effect of ionizing radiation to inhibit tumor growth in vivo. Four groups of chick embryos were studied. The control group did not receive any treatment, a second group received PABA alone, a third group received ionizing radiation alone, and a fourth group received PABA and ionizing radiation. There were 5 to 10 chick embryos in each group.

The groups were created in the following manner. B16F10 melanoma cells were cultured for 14 days in growth medium in the absence of PABA or in the presence of PABA at a concentration of 100 µg/ml. The cells were harvested, washed, and resuspended in sterile PBS. The B16F10 melanoma cells were implanted on the CAMs of 10-day-old chick embryos, which were then incubated for at least 24 hours. The incubated chick embryos (some that were cultured in the absence of PABA and some that cultured in the presence of PABA) were treated with a single fraction dose of ionizing radiation (5.0 Gy). The embryos were incubated for 7 days and then the chick embryos of each group were sacrificed. The tumors were resected and tumor growth was assessed by measuring the wet weights of the resected tumors.

Figure 10:
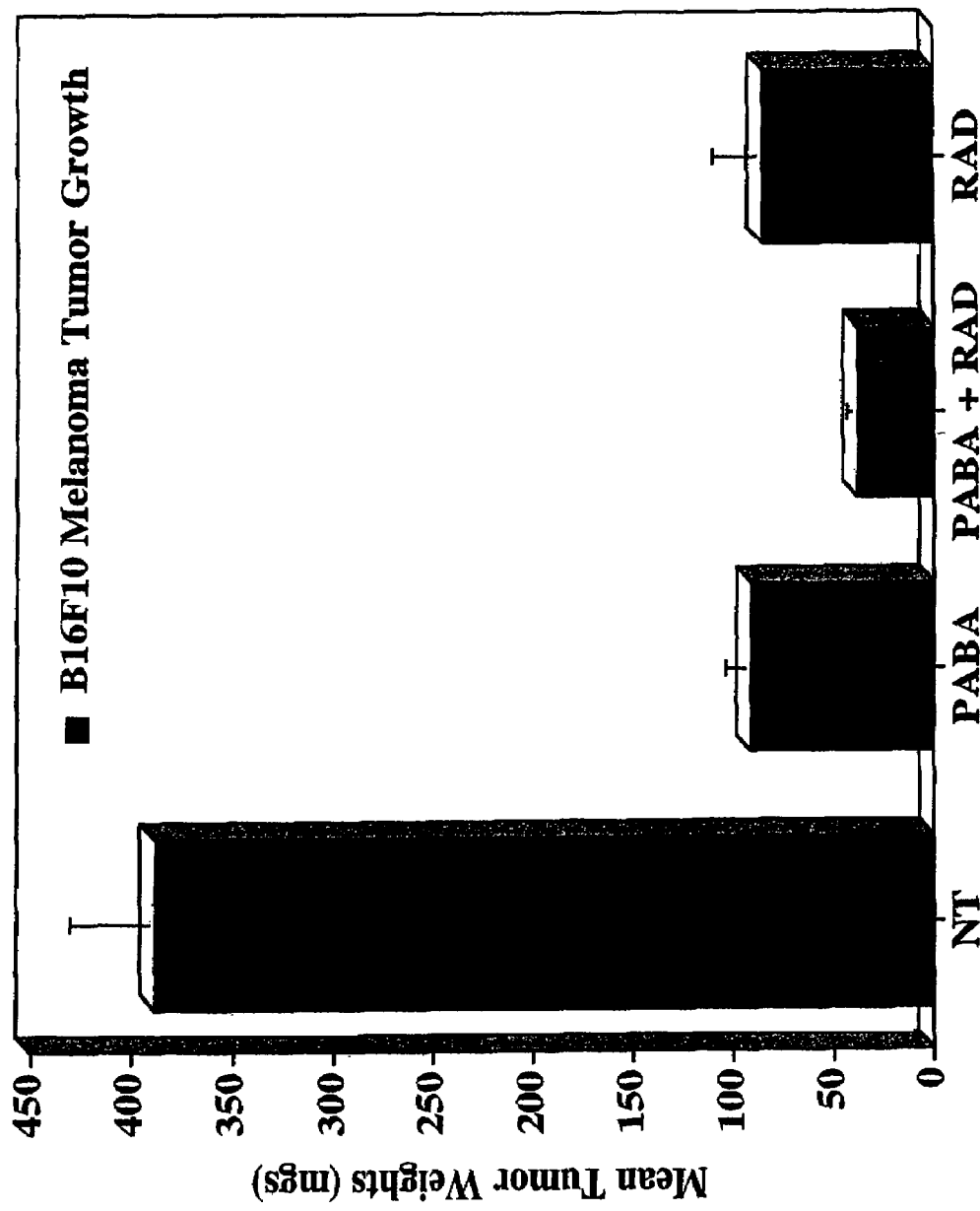
FIG. 10 shows the effect of PABA on the treatment of melanoma with ionizing radiation in an in vivo study of chick embryos.

As shown in FIG. 10, the group that received PABA alone and the group that received radiation alone showed about 75% inhibition of tumor growth as compared to the control group. The group that received both PABA and radiation showed about 90% inhibition of tumor growth as compared to the control group.

This example shows that PABA alone and PABA in combination with radiation therapy result in significant inhibition of melanoma tumor growth in an in vivo model.

Example 13

In Vivo Xenograft Study of PABA and Paclitaxel for the Treatment of Melanoma $1 \times 10^6$ B16F10 melanoma cells (cultured in the absence of PABA) were implanted subcutaneously into Balb/c nude mice. Intraperitoneal injections of PABA at a concentration of 50 mg/kg were started 3 days after implantation of the tumor cells and continued daily. Starting on day 4 post-implantation, some PABA-injected mice and some non-treated mice received intraperitoneal injections of paclitaxel at a concentration of 20 mg/kg, which was continued every other day of the 16 day study. The control group did not receive PABA or paclitaxel. Every 4 days, groups of 10 animals were used for tumor growth assessments starting at day 8.

Figure 11:
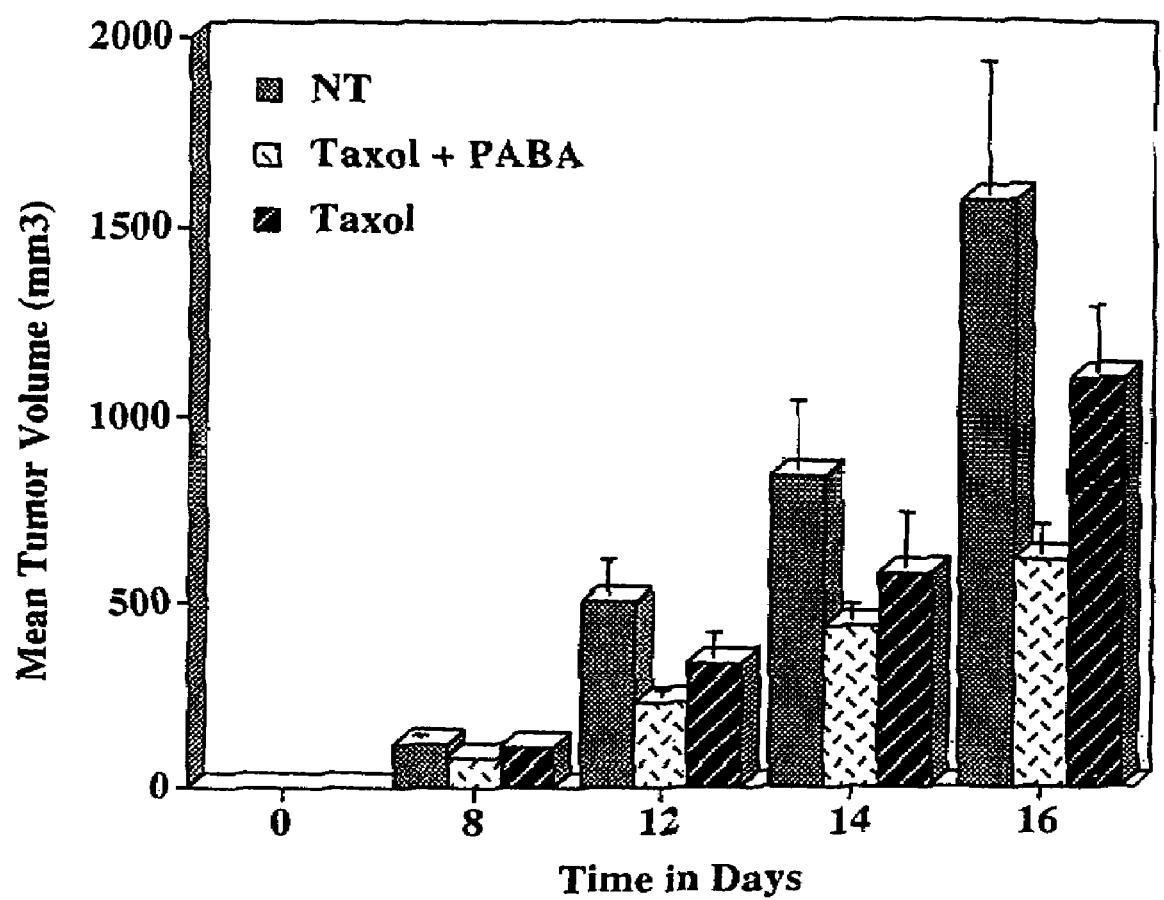
FIG. 11 shows the effect of PABA and paclitaxel on the treatment of melanoma in an in vivo xenograft study of nude (immunodeficient) mice.

At day 12, reduced tumor growth was observed for both the paclitaxel and the paclitaxel plus PABA groups as compared to the control group (FIG. 11). The combination of paclitaxel and PABA showed significant tumor growth retardation with a mean tumor volume of 613±282 mm³. Paclitaxel alone resulted a mean tumor volume of 1097±612 mm³. The mean tumor volume for the control group exceeded 1500 mm³. At day 16, the PABA plus paclitaxel combination group was significantly different form the control group (p=0.016) and the paclitaxel alone group (p=0.045)(Student's t-test for unpaired data).

Example 14

In Vivo Xenograft Study of PABA and Radiation for the Treatment of Melanoma $1 \times 10^6$ B16F10 melanoma cells (cultured in the absence of PABA) were implanted subcutaneously into Balb/c nude mice. Intraperitoneal injections of PABA at a concentration of 50 mg/kg were started 3 days after implantation of the tumor cells and continued daily. Ten days following tumor cell implantation, mice were either not irradiated or were irradiated with 3 fractions of 3 Gy every other day for a total dose of 9 Gy. The control group did not receive PABA or radiation.

Figure 12:
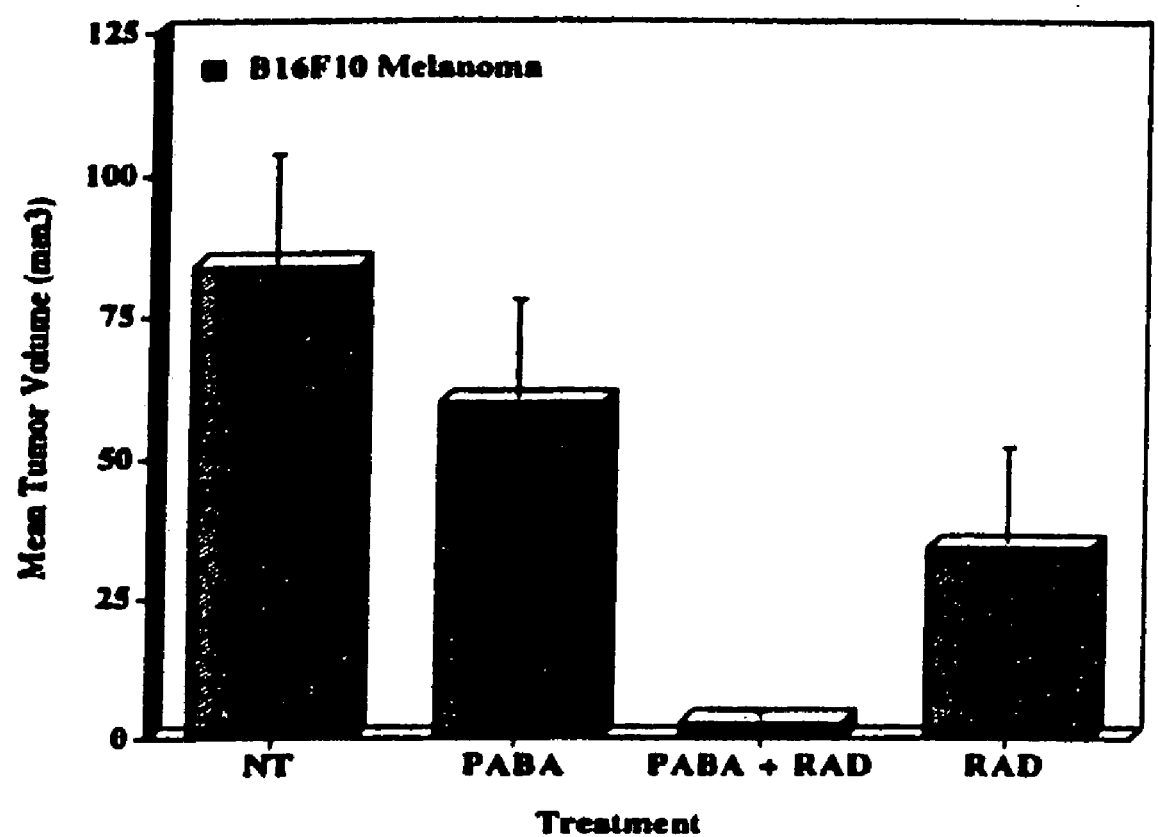
FIG. 12 shows the effect of combination therapy with PABA and radiation on the treatment of melanoma in Balb/c mice.

After 15 days, the animals were sacrificed and the tumors were resected. The tumors were measured and their volumes were calculated. As shown in FIG. 12, PABA alone had a minimal effect on tumor growth as compared to control (P>0.100), fractionated doses of ionizing radiation alone inhibited tumor growth by about 60% as compared to control (P<0.04), and a combination of PABA and fractionated ionizing radiation inhibited tumor growth by about 95% as compared to control (P<0.002).

This example demonstrates that PABA enhances the tumor growth-inhibiting effect of ionizing radiation on melanoma.

Example 15

Treatment of a Patient with Metastatic Malignant Melanoma with a Combination of Carboplatin, Paclitaxel, and PABA A 56 year old woman was diagnosed with malignant melanoma in 1998. A wide surgical excision of her left foot malignant melanoma was performed along with a regional lymph node dissection. The sentinel lymph node (the first lymph node to receive lymphatic drainage from the area of the malignant melanoma) was positive for malignant cells on microscopic examination, but the remaining lymph nodes were negative for malignant cells. The patient declined adjuvant treatment at that time. In 1999, the patient developed a malignant left thigh nodule, which was excised. A work-up for metastatic disease was negative. The patient agreed to adjuvant treatment with interferon. During the sixth month of interferon treatment, the patient developed two malignant subcutaneous left thigh nodules. A six-month treatment with Temodar and thalidomide was undertaken. Following one disease-free year, multiple liver lesions were visualized on routine follow-up CT scans. The patient was restarted on Temodar but her cancer continued to progress.

The patient's treatment was changed to carboplatin. During the second cycle of carboplatin, the patient's colon perforated and an emergency colostomy was performed. Postoperative CT scans in December 2002 showed extensive liver metastases, peritoneal implants (indicative of metastatic lesions on the peritoneum), and bulky retroperitoneal and pelvic lymph nodes (indicative of metastatic spread to these lymph nodes).

Combination chemotherapy with carboplatin, paclitaxel, and PABA was started. PABA was administered at a dose of 2 grams orally for a total of ten days. On the sixth day of PABA administration, carboplatin was administered at a dose calculated according to the Calvert formula with a target AUC of 5 mg/ml*min. Paclitaxel was administered on the sixth day of PABA administration at a dose of 100 mg/m² intravenously. A treatment cycle was completed 21 days after the first administration of PABA. Following an 11 day interval between treatment cycles, another identical treatment cycle was started. A CT scan was performed following three treatment cycles. The patient showed significant clinical improvement and she returned to work in February 2003. CT scans performed in March 2003 showed complete resolution of the liver lesions and a greater than 50% reduction in the intra-abdominal disease.

In August 2003, the patient decided to have her colostomy reversed (an operation in which the continuity of the colon is restored and the colostomy is closed).

The carboplatin, paclitaxel, and PABA combination therapy was stopped for 8 weeks. CT scans prior to surgery showed no change compared to the March 2003 CT scans.

This example demonstrates that combination treatment with carboplatin, paclitaxel, and PABA is effective against metastatic malignant melanoma in a patient whose melanoma both re-occurred following completed chemotherapy and progressed while she on chemotherapy.

The present invention is not to be limited in scope by the specific embodiments described herein. Various modifications of the invention in addition to those described herein will become apparent to those skilled in the art from the foregoing description and the accompanying figures. Such modifications are intended to fall within the scope of the appended claims.

The complete disclosure of all patents, patent applications, publications, procedures, and the like cited throughout this application, are incorporated herein by reference in their entireties. In the case of inconsistencies in definitions, the present application is controlling.

We claim:

1. A method for treating a patient with malignant melanoma comprising administering a combination of carboplatin, paclitaxel, and p-aminobenzoic acid (PABA) to the patient with malignant melanoma.

2. The method of claim 1 wherein the patient with malignant melanoma has metastatic malignant melanoma.

3. The method of claim 1 wherein the patient with malignant melanoma has recurrent malignant melanoma.

4. The method of claim 1 wherein the patient with malignant melanoma has non-responsive malignant melanoma.

* * * * *